United States Patent [19]
Michael

[11] Patent Number: 5,250,049
[45] Date of Patent: Oct. 5, 1993

[54] BONE AND TISSUE CONNECTORS

[76] Inventor: Roger H. Michael, 3428 Uniontown Rd., Uniontown, Md. 21157

[21] Appl. No.: 819,175

[22] Filed: Jan. 10, 1992

[51] Int. Cl.$^5$ .................. A61B 17/56; F16B 21/00
[52] U.S. Cl. .................................. 606/72; 606/77; 411/908
[58] Field of Search ............ 606/60, 62, 72, 73, 606/74, 75, 77; 24/16 PB, 16 R, 17 AP, 277, 279; 411/366, 392, 437, 527, 908

[56] References Cited

U.S. PATENT DOCUMENTS

| | | | |
|---|---|---|---|
| 3,072,986 | 1/1963 | Lefnaer | 24/16 PB |
| 3,111,945 | 11/1963 | Solbrig | 606/74 |
| 3,469,573 | 9/1969 | Florio | 606/74 |
| 3,576,054 | 4/1971 | Rynk | 606/74 |
| 3,964,133 | 6/1976 | Wasserlein | 24/16 PB |
| 4,009,509 | 3/1977 | McCormick | 24/16 PB |
| 4,119,091 | 10/1978 | Partridge | 606/74 |
| 4,535,764 | 8/1985 | Ebert | 606/74 |
| 4,679,548 | 7/1987 | Pecheux | 128/26 |
| 4,688,561 | 8/1987 | Reese | 606/72 |
| 4,813,416 | 3/1989 | Pollak | 606/74 |
| 5,059,193 | 10/1991 | Kuslich | 606/62 |

Primary Examiner—Michael A. Brown
Attorney, Agent, or Firm—S. Michael Bender

[57] ABSTRACT

Bone and tissue connectors are designed for use on or in the human body for the purpose of connecting bone or soft tissue to promote a healing process. Various embodiments are in the form of bands, straps, braids, or rods and are secured by fasteners such as pegs, plates, screws and cable ties. All of the connectors are formed from materials having a similar modulus of elasticity as bone and include, among others, polyethylene, polysulfone, collagen and polymer-carbon fiber composites.

3 Claims, 9 Drawing Sheets

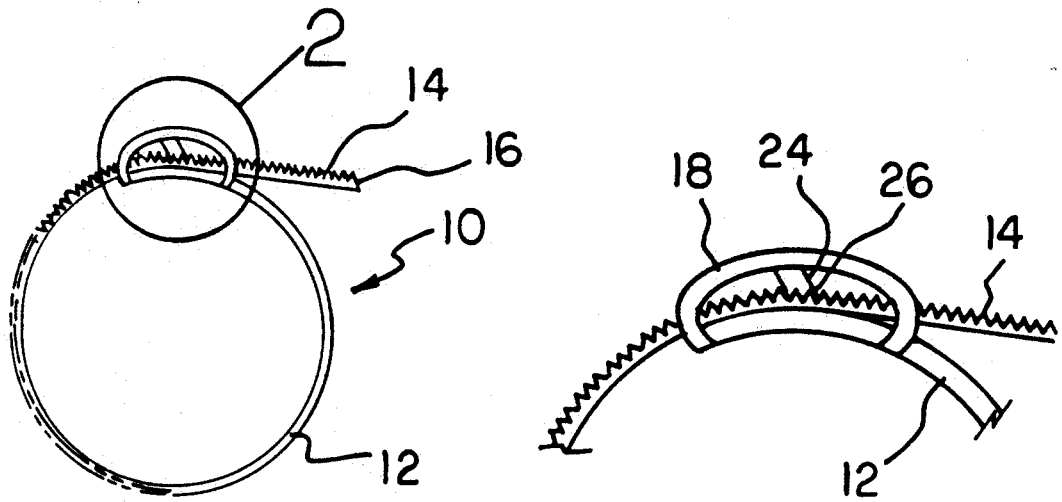
FIG 1
FIG 2
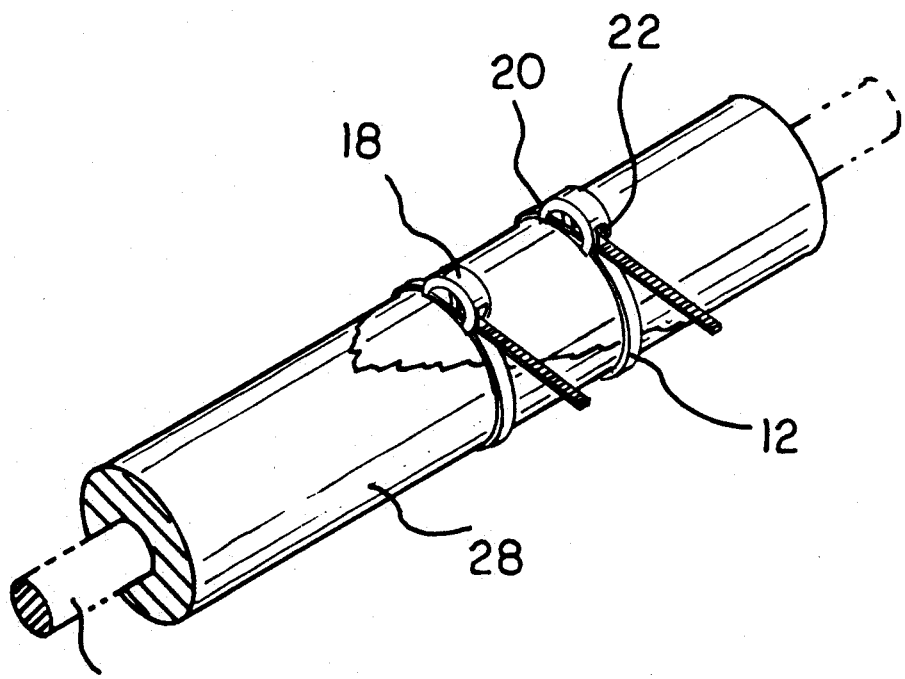
FIG 3

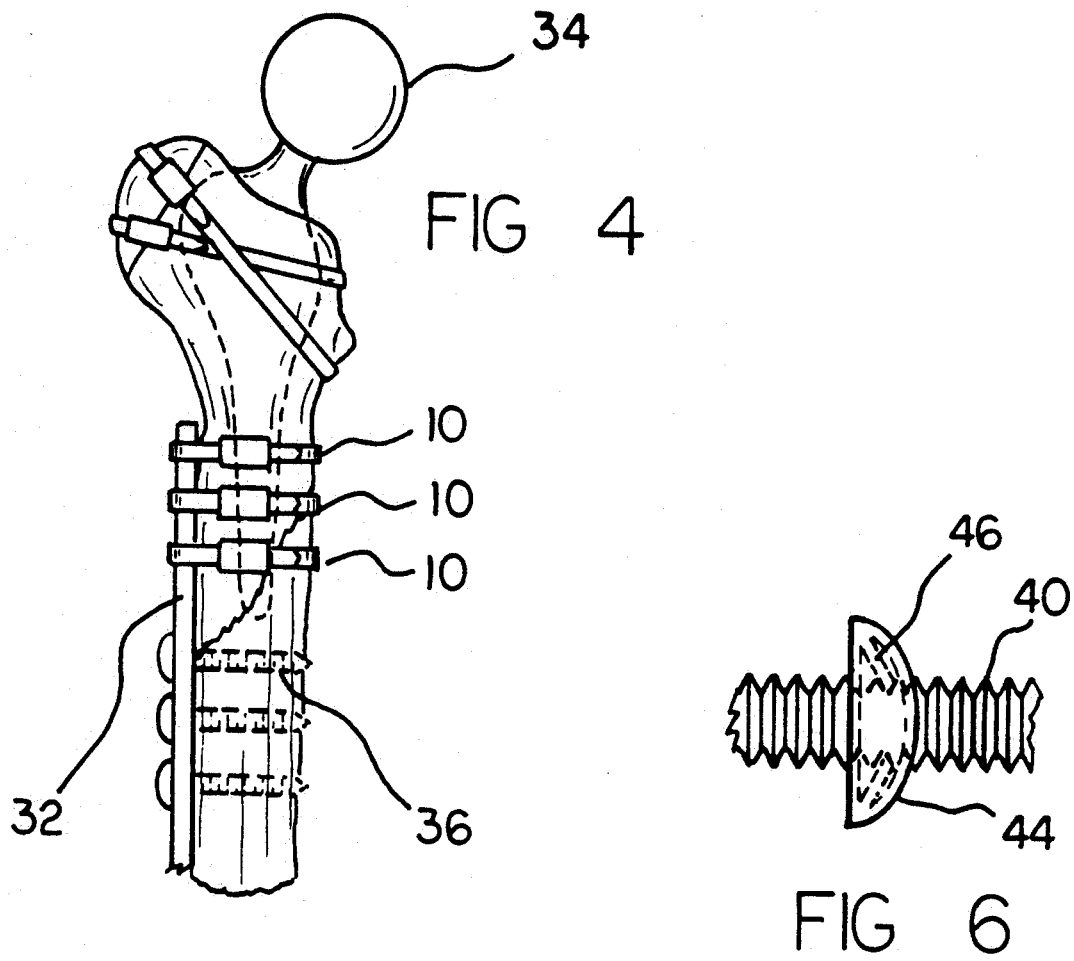
FIG 4
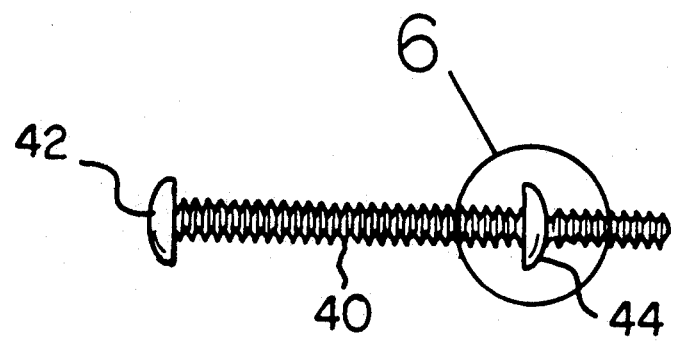
FIG 6
FIG 5

BONE AND TISSUE CONNECTORS

BACKGROUND OF THE INVENTION

1. Field of the Invention

The present invention relates to medical devices and more particularly pertains to various connectors designed to facilitate the healing of broken bones or torn tissue in the human body.

2. Description of the Prior Art

There is a plethora of well known devices used in the medical field for the purpose of temporarily connecting broken bones and torn tissue. Most of these devices rely upon implantable rods positionable within a broken bone, bone and tissue plates attachable to external surfaces of the bones and tissue, and surgical steel screws designed to attach plates or otherwise hold broken bones together by a threaded attachment arrangement. These various devices are constructed out of conventional materials such as stainless steel, titanium, and chrome cobalt alloys. These rigid materials will often cause atrophy of a broken bone which frequently then results in the necessity of having a second medical operation.

A typical example of a bone implant is to be found in U.S. Pat. No. 4,787,378 which issued to Jitendra Sodhi on Nov. 29, 1988. This patent discloses a self-retaining nail which is inserted inside a broken femur so as to urge the two bone halves together, thereby facilitating a healing by a natural growth process.

Another patent of interest as disclosing a bone implant is U.S. Pat. No. 4,955,911 which issued to Frey et al. on Sep. 11, 1990. This patent is of interest inasmuch as the bone implant is formed of a plastic body having a multi-layer wire fabric secured to an outside surface. As such, some flexible movement of the bone implant is facilitated and this is a desirable characteristic in the healing process. However, this type of implant would most likely be difficult and costly to manufacture which perhaps accounts for its unavailability at the present time in the commercial market.

U.S. Pat. No. 4,943,292, which issued to Amnon Foux on Jul. 24, 1990, is of interest as disclosing a plate positionable on an external surface of a broken bone and which utilizes the aforediscussed surgical screws. These screws are positioned in elongated holes filled with an elastically deformable material whereby the plate is utilized to stabilize the bone pieces but permits the screws, and hints the bone pieces, to move a short distance back and forth in the direction of the axis of the bone in order to promote healing.

A typical example of a plate for broken bone fixation is disclosed in U.S. Pat. No. 4,429,690 which issued to Giancarlo Angelino-Pievani on Feb. 7, 1984. This patent is representative of a plurality of prior art patents which disclose various configurations for rigid bone-holding plates.

Another patent which is of interest and which relates to a bone plate is U.S. Pat. No. 4,905,680 which issued to Degar Tunc on Mar. 6, 1990. This patent discloses an absorbable bone plate which is constructed totally of materials that will eventually be absorbed in the body.

As can be appreciated, all of the above-discussed bone fixation devices are functional for their intended purposes and there is a distinct possibility that all are now being used at various times. However, as can also be appreciated, there is a continuing need for new and improved bone and tissue fixation devices which represent a simpler and less costly construction while facilitating an enhanced degree of reliability. In this respect, the various embodiments of the present invention substantially fulfill this need.

SUMMARY OF THE INVENTION

In view of the foregoing disadvantages inherent in the known types of bone and tissue fixation devices now present in the prior art, the present invention provides various embodiments of improved bone and tissue fixation devices to thus reduce the cost of manufacture and difficulty of use thereof. As such, the general purpose of the present invention, which will be described subsequently in greater detail, is to provide new and improved bone and tissue fixation devices which have all the advantages of the prior art bone and tissue fixation devices and none of the disadvantages.

To attain this, the present invention essentially comprises bone and tissue connectors which are designed for use on or in the human body for the purpose of connecting bone or soft tissue to promote a healing process. Various embodiments are in the form of bands, straps, braids, or rods and are secured by fasteners such as pegs, plates, screws and cable ties. All of the connectors are formed from materials having a similar of elasticity as bone and include, among others, polyethylene, polysulfone, collagen and polymer-carbon fiber composites.

In this regard, the bone and tissue fixation devices comprising the present invention are non-toxic and biocompatible, while also being strong, lightweight and flexible as opposed to the aforediscussed conventional materials (stainless steel, titanium and chrome cobalt alloys) currently used for the same purpose. All of these fixation devices can be produced at a reasonable cost, and their applications in world wide orthopedic surgery are unlimited.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved bone and tissue fixation devices which have all the advantages of the prior art bone and tissue fixation devices and none of the disadvantages.

It is another object of the present invention to provide new and improved bone and tissue fixation devices which ay be easily and efficiently manufactured and marketed.

It is a further object of the present invention to provide new and improved bone and tissue fixation devices which are of a durable and reliable construction.

An even further object of the present invention is to provide new and improved bone and tissue fixation devices which are susceptible of a low cost of manufacture with regard to both materials and labor, and which accordingly are then susceptible of low prices of sale to the consuming public, thereby making such bone and tissue fixation devices economically available to the buying public.

Still yet another object of the present invention is to provide new and improved bone and tissue fixation devices which provides in the apparatuses and methods of the prior art some of the advantages thereof, while simultaneously overcoming some of the disadvantages normally associated therewith.

Still another object of the present invention is to provide new and improved bone and tissue fixation devices which are constructed of material having similar modulus of elasticity as a human bone.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevation view of a flat cable tie comprising a first embodiment of the present invention.

FIG. 2 is an enlarged detail view taken from FIG. 1.

FIG. 3 is a perspective view illustrating a use of the first embodiment of the invention.

FIG. 4 is an elevation view illustrating a plate and cable tie combination which comprise a second embodiment of the invention.

FIG. 5 is a front elevation view of a round cable tie comprising a third embodiment of the invention.

FIG. 6 is an enlarged detail view of the invention taken from FIG. 5.

DESCRIPTION OF THE PREFERRED EMBODIMENTS

Figure 7:
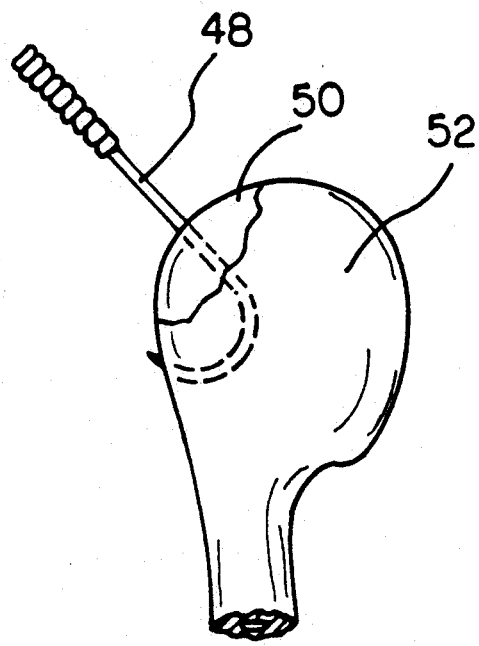
FIG. 7 is a perspective view illustrating a manner of forming an aperture to facilitate a use of the third embodiment of the invention.

With reference now to the drawings, and in particular to FIGS. 1-3 thereof, a first embodiment of a new and improved bone and tissue fixation device embodying the principles and concepts of the present invention and generally designated by the reference numeral 10 will be described.

More specifically, it will be noted that the first embodiment 10 of the invention comprises a flat, flexible band 12 formed from a material having similar modulus of elasticity as a human bone. These materials include but are not limited to polyethylene, polysulfone, collagen and polymer-carbon. In this regard, all embodiments of the invention as will be subsequently described will include a use of these modulus-matching materials to the fullest extent possible.

The flat flexible band 12 has a plurality of upstanding integral teeth 14 molded into a first free end 16, and the second end of the band includes an integral upstanding curvilinearly-shaped member 18 which has first and second openings 20, 22 through which the end 16 of the band 12 can be positioned as best illustrated in FIGS. 2 and 3. Attached to an interior top portion of the member 18 is an angulated, downwardly positioned spring member 24 having a serrated end 26 which is symmetrically positionable within the teeth 14. The spring member 24 is of a fail proof construction and might in a preferred embodiment be constructed from surgical steel.

The spring member 24 can flexibly bend to allow the teeth 14 to be pulled through the opening 20, 22 so as to effect a tightening of the clamp around a broken bone 28 as best illustrated in FIG. 3. The angulated forward positioning of the spring 24 facilitates the flexible movement of the teeth 14 as they slide through the openings 20, 22 while at the same time preventing a reverse movement of the teeth and a subsequent loosening of the band 12 after a desired degree of tightening has been achieved. The member 18 effectively comprises a low profile head so that the cable tightener 10 is of a desirable medical grade and as shown in FIG. 3, an optional composite rod 30 might be positioned within a broken bone 28 prior to the use of one or more of the flat cable ties 10.

FIG. 4 of the drawings illustrates a modified embodiment of the flat cable tie 10 wherein the same is utilized with a flat bar member 32 constructed from the above-mentioned material. The bar member 32 is particularly useful when a prosthesis 34 is used to construct a hip joint or the like and threaded screws 36 cannot be employed to attach the bar in the area of the prosthesis. More particularly, threaded fasteners 36 would come into contact with the prosthesis 34 as can be seen in FIG. 4, so this form of the invention is combined with a plurality of flexible cable ties 10 to effectively hold the broken bone together.

FIGS. 5 and 6 of the drawings illustrate a third embodiment of the invention that effectively comprises a flexible round cable tie which is generally designated by the reference numeral 38. The tie 38 includes a notched round band 40 having a fixed head 42 attached thereto. A moveable head 44 is selectively moveable by advancement along the band member 40, and upstanding spring locks 46 positioned within the concavely shaped moveable head 44 serve to hold the moveable head in fixed engagement with the shank 40 after the desired position has been achieved. More specifically, the spring locks 46 can be constructed from a fail proof material, such as stainless steel or the like, and are sloped to allow movement of the moveable head 44 on the shank 40 while then serving to frictionally engage the shank by spring lock to prevent a loosening movement of the moveable head.

Figure 8:
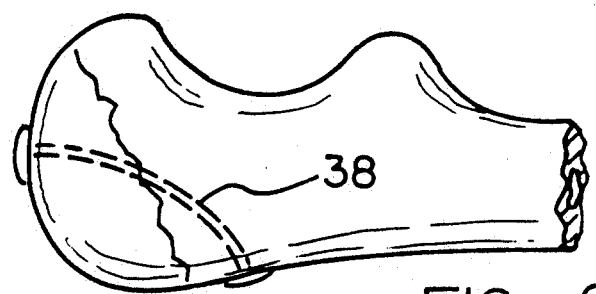
FIG. 8 is a perspective view illustrating a first use of the third embodiment of the invention.
Figure 9:
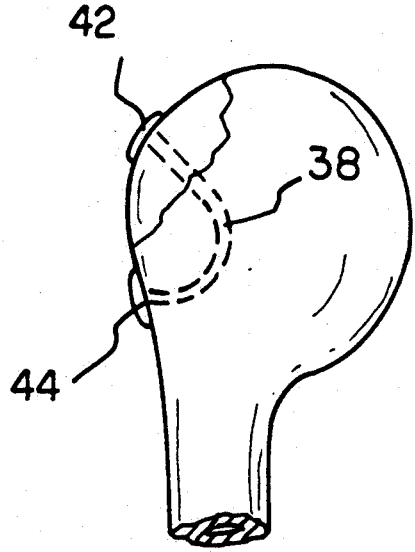
FIG. 9 is a perspective view illustrating a second use of the third embodiment of the invention.

FIGS. 7, 8 and 9 illustrate a manner of usage of the flexible round cable tie 38. In this respect, FIG. 7 shows a broken humerus bone, and a semi-rigid awl 48 is used to hone out a drilled aperture extending through the two broken, mating pieces of bone 50, 52. The flexible tie 38 can then be positioned through the curvilinearly-directed aperture as shown in FIG. 9 and the excess shank 40 can be clipped off proximate the moveable head 44 which is now locked in position. Of course, as illustrated in FIG. 8, the flexible round tie member 38 can be used on any type of bone break such as the head of an ulna.

Figure 10:
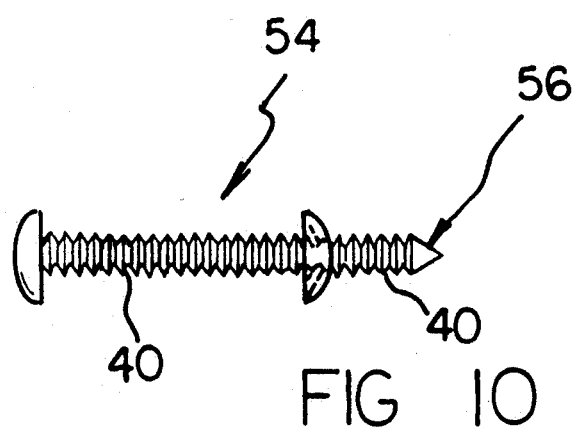
FIG. 10 is an elevation view illustrating a round cable tie comprising a fourth embodiment of the invention.

FIG. 10 illustrates a modified embodiment of the flexible round cable tie 38 with this modified embodiment being generally designated by the reference numeral 54. As illustrated, the embodiment 54 is identical in all respects to the embodiment 38 of the invention with the exception that the notched shank member 40 is provided with an integral pointed end 56 which facilitates its forced movement through a drilled aperture in a bone. Depending upon the rigidity of the shank 40 in the embodiment 54 of the invention, the pointed end 56 could be utilized to expand an existing aperture or even create a new one.

Figure 11:
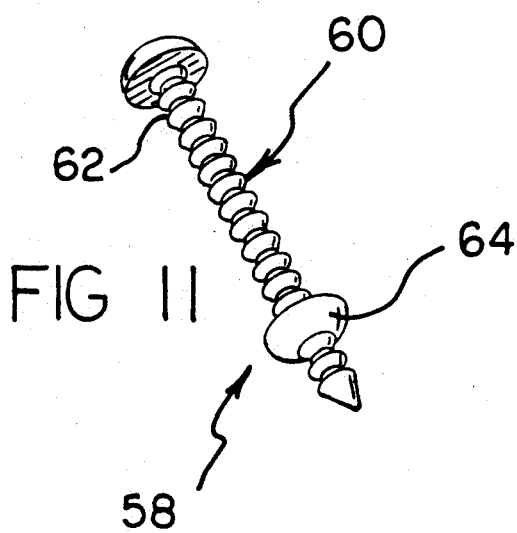
FIG. 11 is a perspective view of a round cable tie comprising a fifth embodiment of the invention.
Figure 12:
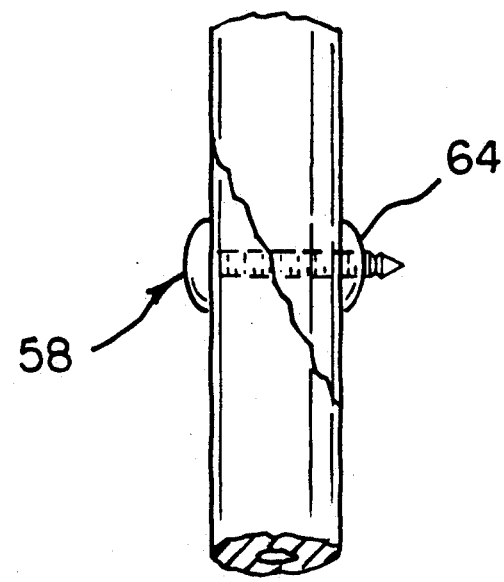
FIG. 12 is a perspective view illustrating a use of the fourth and fifth embodiments of the invention.

FIGS. 11 and 12 of the drawings illustrate a fifth embodiment of the invention which is generally designated by the reference numeral 58. The embodiment 58 also comprises a round cable tie similar to the embodiment 54, with the exception that the notched shank 40 has been replaced with a shank 60 having a plurality of circumferentially extending detents 62, and the moveable head 64 is then forcibly positioned over each of the cup-shaped detents. More specifically, the circumferentially extending detents 62 are flexibly mendable in response to a forced movement of the moveable head 64 thereover and are provided with enough elasticity to return to their normal shape thereafter so as to prevent a reverse movement of the moveable head 64 down the shank 60. This type of fastener 58 is particularly useful, as shown in FIG. 12, in those areas of a bone break where it is difficult to effect a threadable movement of either the fixed head associated with the tie 58 or the moveable head 64 attached thereto.

Figure 13:
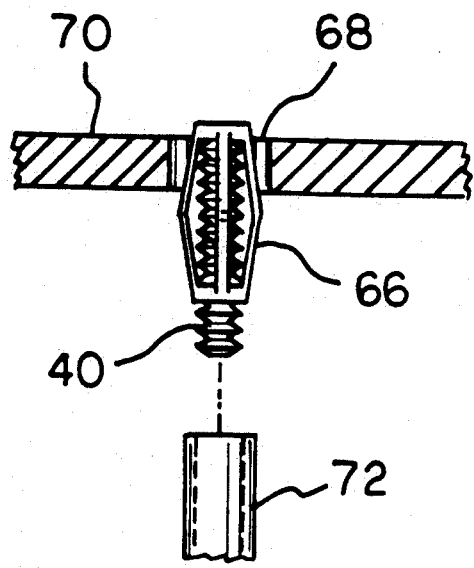
FIG. 13 is an elevation view illustrating a cable tie having a deployable head which comprises a sixth embodiment of the invention.
Figure 14:
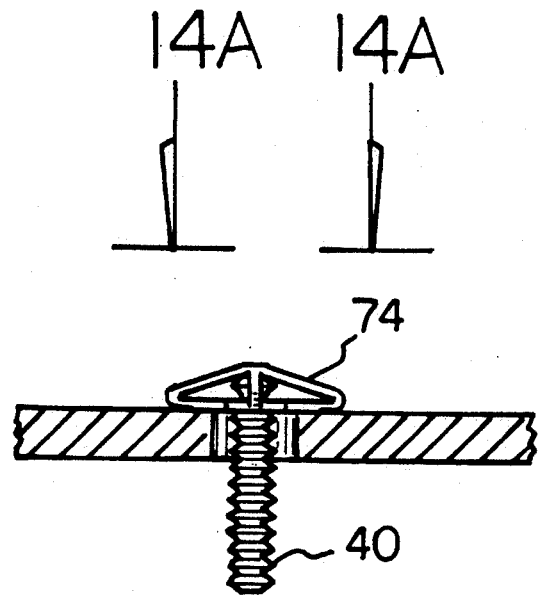
FIG. 14 is an elevation view illustrating the sixth embodiment of the invention in a deployed condition.
Figure 14A:
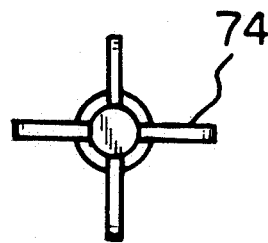
FIG. 14A is a top plan view of the sixth embodiment of the invention as viewed along the line 14A—14A in FIG. 14.

Another alternative to those situations where a moveable head cannot be threadably attached to a shank 40 is illustrated in FIGS. 13, 14 and 14A. In this regard, the shank 40 is provided with a deployable head 66 which effectively comprises a stainless sleeve-shaped spring and which may be forced through an opening 68 in a bone 70 as best shown in FIG. 13 by use of some type of deploying instrument 72. Once the deployable head 66 has cleared the opening 68, a reverse movement of the shank 40 will result in the head collapsing into the cross-shaped position 74 as illustrated in both FIGS. 14 and 14A. As can be appreciated, the deployable head 66 is fixedly secured to a free end of the shank 40, and the reverse movement force effectively collapses the head into the position 74 best illustrated in FIG. 14.

Figure 15:
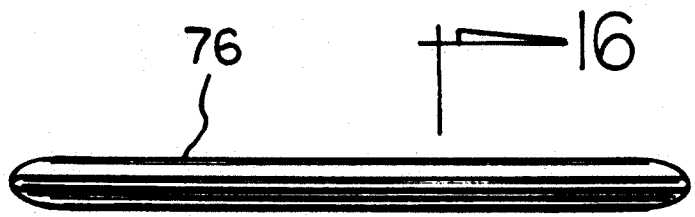
FIG. 15 is a front elevation view of a peg comprising a seventh embodiment of the invention.
Figure 16:
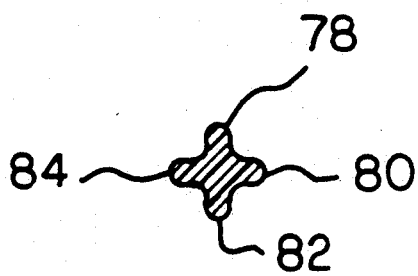
FIG. 16 is a cross-sectional view of the peg shown in FIG. 15 as viewed along the lines 16—16 thereof.
Figure 17:
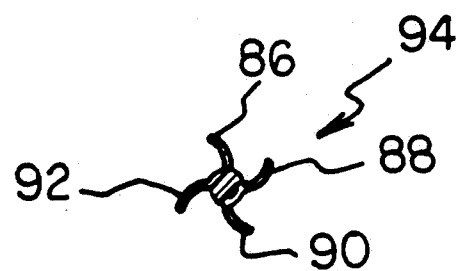
FIG. 17 is a cross-sectional view of the peg shown in FIG. 15 illustrating a modified embodiment thereof which effectively comprises the eighth embodiment of the invention.
Figure 18:
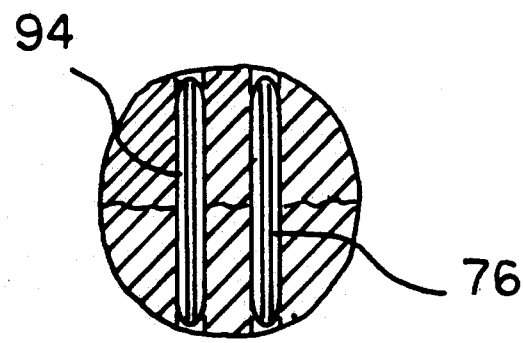
FIG. 18 is a cross-sectional view illustrating a use of the seventh and eighth embodiments of the invention.
Figure 19:
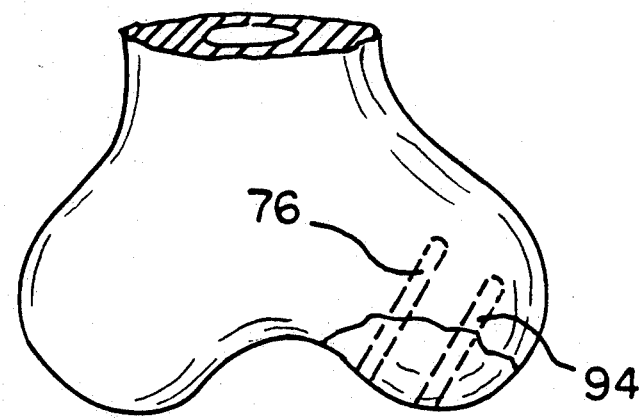
FIG. 19 is a perspective view illustrating a further use of the seventh and eighth embodiments of the invention.

The present invention also envisions the use of force fittable pegs 76 of the type illustrated in FIGS. 15 and 16. Recognizing that the peg 76 is of a somewhat flexible construction and possesses similar modulus of elasticity of a human bone, a "plus" shaped cross-section facilitates a tight fit of such a peg between mating bone halves. While the peg 76 is shown as having four axially aligned ridges 78, 80, 82, 84 in FIG. 16, it could also have substantially flexible, curvilinearly shaped ridges 86, 88, 90, 92 as shown in FIG. 17. This embodiment shown in FIG. 17 is generally designated by the reference numeral 94 and facilitates a more easily placed positioning of a peg in a manner which can now be well understood. In this regard, FIGS. 18 and 19 illustrate two preferred uses of the pegs 76, 94. Specifically, either of the peg embodiments 76, 94 can be used in a broken patella (knee cap) as shown in FIG. 18 or, for example, in a broken femur wherein the pegs would be inserted with an arthroscope as best illustrated in FIG. 19.

Figure 20:
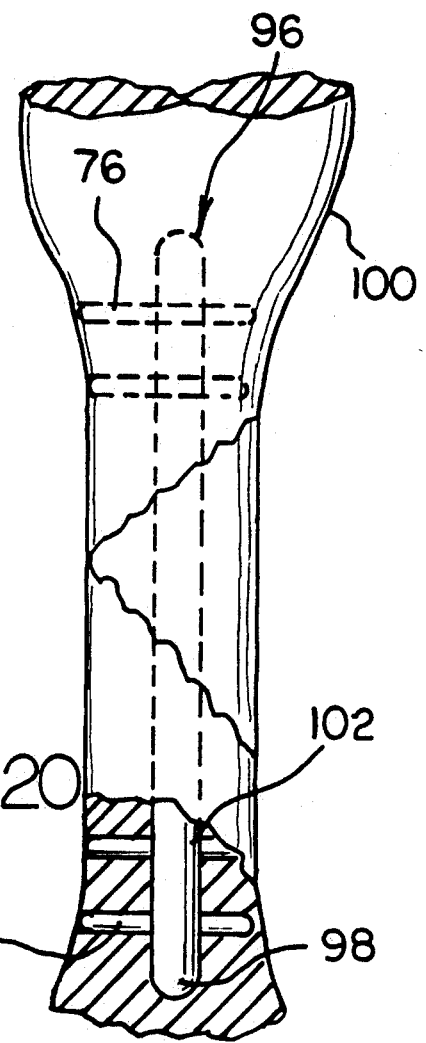
FIG. 20 is an elevation view, partly in cross-section, illustrating a peg and rod combination which comprises a ninth embodiment of the present invention.

FIG. 20 of the drawings illustrates a modified embodiment of the invention which is generally designated by the reference numeral 96. In this embodiment 96, any combination of the pegs 76, 94 can be employed with a composite rod 98 positionable within a broken bone 100. As shown, the pegs 76, 94 can be positioned through a plurality of laterally extending apertures 102 formed in the composite rod 98, and such positioning of the pegs prevent a shortening of the rod or associated bone, as well as rotation of the rod within the bone during the healing process.

Figure 21:
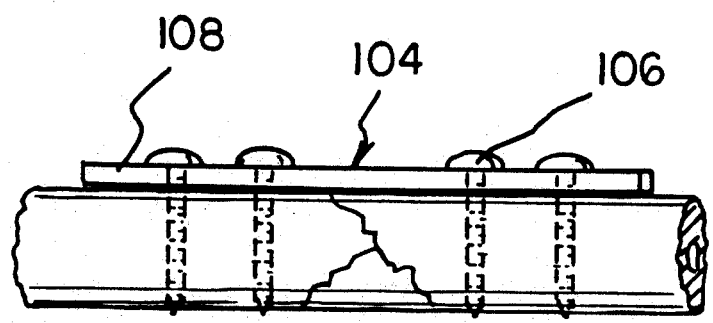
FIG. 21 is a perspective view illustrating a plate and screw combination which comprises a tenth embodiment of the present invention.

FIG. 21 of the drawings illustrates a further embodiment of the invention 104 wherein screws 106 formed of a material having a similar modulus of elasticity as the bone are positionable through a plate 108 also formed of that material. In this embodiment 104, the plate 108 may be contoured to a selected shape to match the bone structure, and it is envisioned that a microwave oven or some similar heater could be utilized to soften the plate prior to its being molded to such a desired shape.

Figure 22:
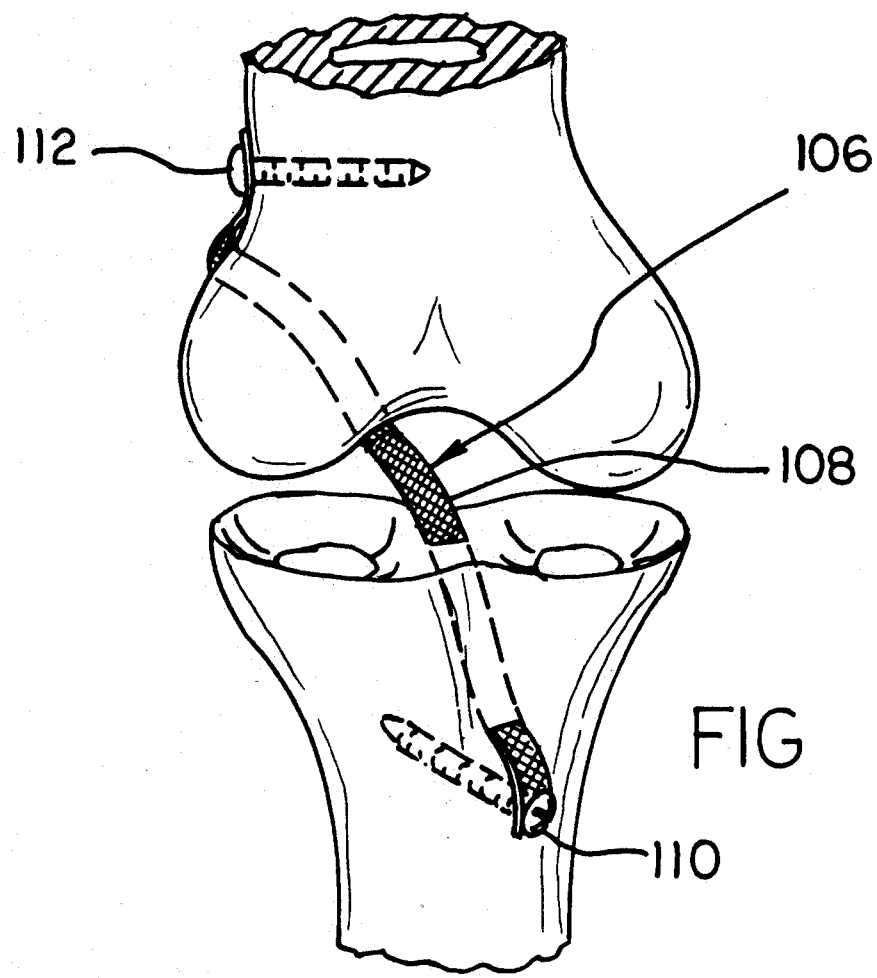
FIG. 22 is a perspective view illustrating a flexible braid utilizable as a substitute for a human ligament and effectively comprising a eleventh embodiment of the present invention.

FIG. 22 of the drawings illustrates a further embodiment of the invention 106 wherein the selected material is braided to effectively create a very flexible band 108 having threaded fasteners 110, 112 attached to the free ends thereof. The braid 106 is illustrated as being utilized to repair ligament damage in a knee joint. The braided band 108 can function as a primary ligament or augment the strength of an existing ligament. It is envisioned that the braid 108 would be attached proximate to an existing or missing ligament in a now well understood manner.

Figure 23:
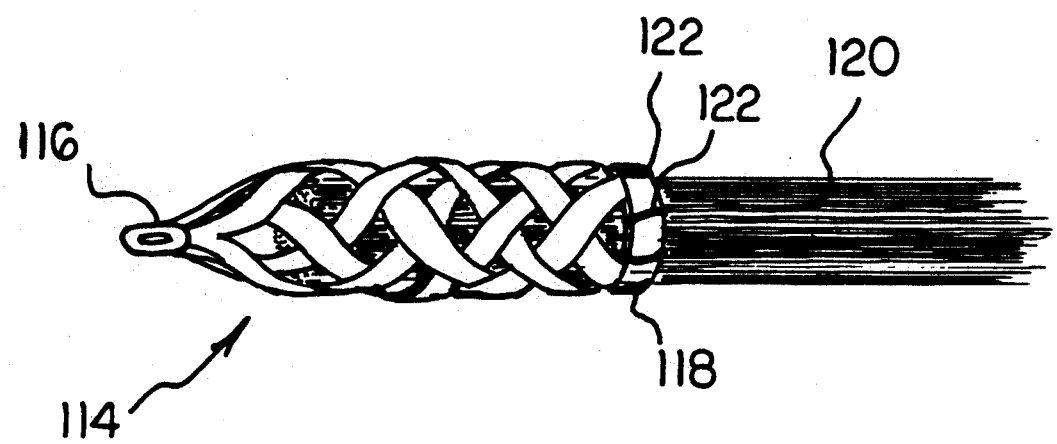
FIG. 23 is a perspective view illustrating a flexible chinese trap utilized for tendon repair with such trap comprising a twelfth embodiment of the present invention.

FIG. 23 of the drawings illustrates a use of the same flexible braid material 108 with it being formed into a chinese trap structure 114. A connection loop 116 is positionable at one end of the chinese trap 114 and a circular band 118 is located at the other end. The band 118 is positionable over a torn ligament or tendon 120, and a chinese trap structure 114 is then collapsed to grasp the tendon or ligament. A plurality of sutures 122 may also be employed to keep the chinese trap structure 114 in position, and it can then be fastened to a bone through the use of an appropriate connector positioned through the opening 116.

Figure 24:
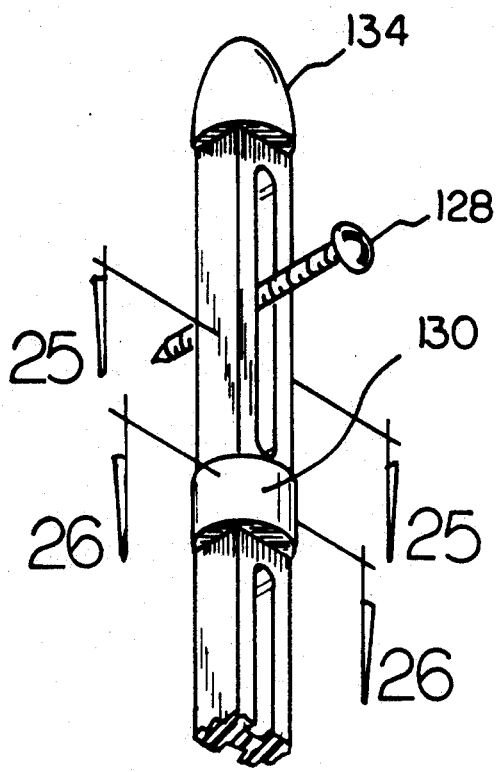
FIG. 24 is an exploded perspective view, partially in cross-section, illustrating an intramedullary rod comprising a thirteenth embodiment of the present invention.
Figure 24:
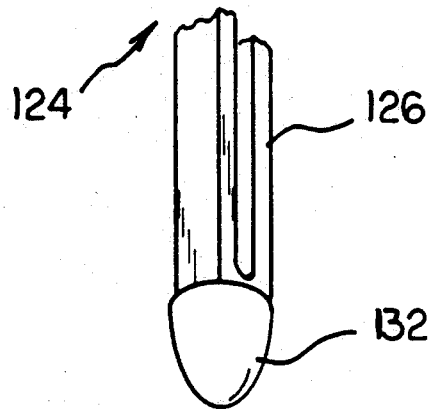
Figure 25:
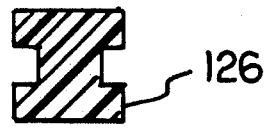
FIG. 25 is a cross-sectional view of the invention as viewed along the line 25—25 in FIG. 24.
Figure 26:
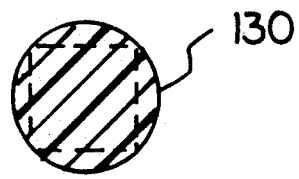
FIG. 26 is a cross-sectional view as viewed along the line 26—26 in FIG. 24.
Figure 27:
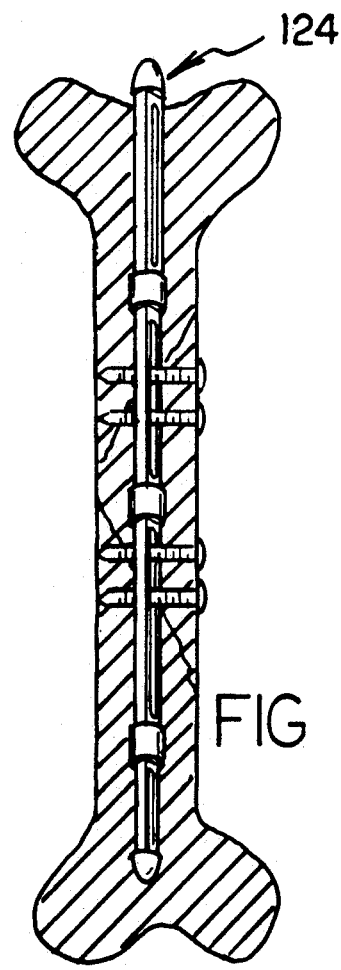
FIG. 27 is a cross-sectional view illustrating a use of the thirteenth embodiment of the invention.

FIGS. 24, 25 and 26 illustrate a specially designed intramedullary rod concept which is generally designated by the reference numeral 124 and which essentially comprises a nonmetallic rod of a slightly flexible construction formed from the same materials as the previous embodiments of the invention. The rod 126 is of a general I-beam construction so as to provide strength, and threadable fasteners 128 may be drilled through the rod at desired locations. Integral or separable rings 130 may be positioned at various points along the rod 126 to provide further strength, and the ends 132, 134 of the rod are smoothly curved to allow easy insertion within a hollow bone as best illustrated in FIG. 27. This rod structure 134 is used to link fragments or segments of bone, and the rod effectively acts as a "core" to which other devices may be attached, i.e., the aforementioned pegs, screws, nails, straps, etc.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved orthopedic fixation device comprising a connector adapted to hold pieces of bone or other body tissue together during a healing phase, said connector having a body portion and means for attaching said body portion to said bone pieces or other body tissue, said connector being of a material having substantially the same modulus of elasticity as said bone or other tissue wherein said material is selected from the group consisting of polyethylene, polysulfone, collagen, or polymer-carbon, wherein said body portion comprises a flexible rod having a round cross-section, a first head portion fixed integrally at one end thereof opposite a free end of said rod, a series of circumferentially extending stop means disposed axially along said rod, and a second movable head portion having an aperture therein for receiving said free end of said rod, and locking means positioned inside of said aperture of said second movable head portion for engaging said stop means as said second head portion is moved axially along said rod in the direction of said first head portion.

2. The orthopedic fixation device of claim 1 wherein said stop means disposed along said rod comprises flexible circumferentially extending ridges adapted to pass through said aperture and prevent movement of said second head portion in the direction of said free end of said rod.

3. The orthopedic fixation device of claim 2 wherein said second movable head portion comprises a collapsible sleeve captured on said flexible rod.

* * * * *